United States Patent [19]

Sucher

[11] Patent Number: 5,468,220
[45] Date of Patent: Nov. 21, 1995

[54] CARPAL TUNNEL BRACELET

[76] Inventor: Benjamin M. Sucher, 5261 E. Fanfol Dr., Paradise Valley, Ariz. 85253

[21] Appl. No.: 395,120

[22] Filed: Feb. 27, 1995

[51] Int. Cl.$^6$ .................................................. A61F 5/00
[52] U.S. Cl. ........................... 602/21; 63/8; 63/9; 2/170; 606/201
[58] Field of Search .................... 602/21, 40, 64; 606/201–204; 128/878, 879; 2/170, 162; 63/2, 3, 7–9

[56] References Cited

U.S. PATENT DOCUMENTS

| Re. 34,627 | 5/1994 | Davini | 2/170 X |
|---|---|---|---|
| 244,687 | 7/1881 | Thiery | 63/8 |
| 515,367 | 2/1894 | Rounseville | 606/203 |
| 993,305 | 5/1911 | Kirby | 63/8 |
| 1,473,041 | 11/1923 | Henderson | 606/203 |
| 3,595,225 | 7/1971 | Beeman | 602/21 |
| 3,884,240 | 5/1975 | Gilman | 606/201 |
| 4,294,237 | 10/1981 | Frazier | 602/21 |
| 4,662,364 | 5/1987 | Viegas et al. | 602/21 |
| 5,295,996 | 3/1994 | Blair | 606/203 |

OTHER PUBLICATIONS

"The Use of Spring Loaded Splints . . . ", Plastic and Reconstructive Surgery, Jun. 1982, pp. 1015–1016.
"Case Studies: Contracture and Stiff Joint Management with Dynasplint™" The Journal of Orthopedic and Sports Physical Therapy, Apr. 1987 pp. 498–504.

*Primary Examiner*—Linda C. M. Dvorak
*Attorney, Agent, or Firm*—Cahill, Sutton & Thomas

[57] ABSTRACT

A bracelet-like appliance for the treatment or prevention of carpal tunnel syndrome includes a C-shaped member having a central portion located over the dorsal side of the wrist and two arms encircling the wrist. Each arm has a pad for engaging the palm near the attachment edges of the carpal ligament at the medial border and the lateral border of the carpal bones. The bracelet also includes a pad attached to the central portion for engaging the dorsal part of the wrist. The member is shaped to cause the pad attached to the central portion to press against the dorsal side of the wrist while the ends of each arm press in the opposite direction on the edges of the palm. The C-shaped member is a single piece of resilient, malleable material, such as aluminum, or is divided into sections interconnected by spring loaded hinges.

7 Claims, 2 Drawing Sheets

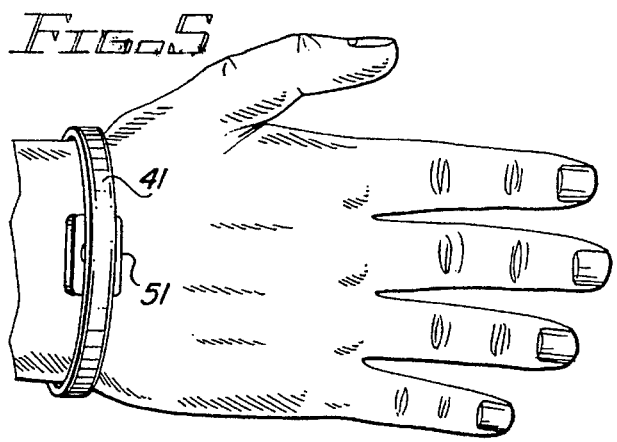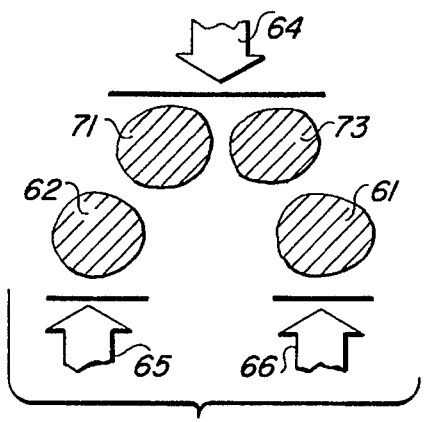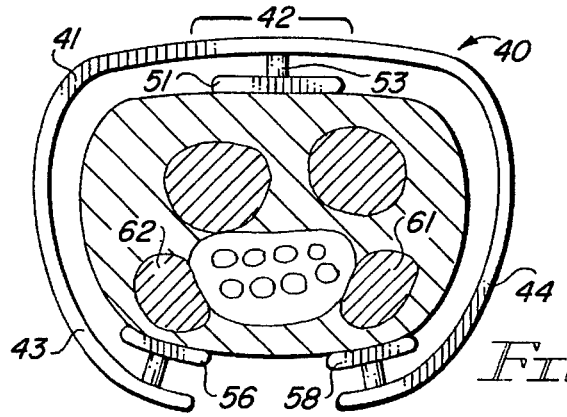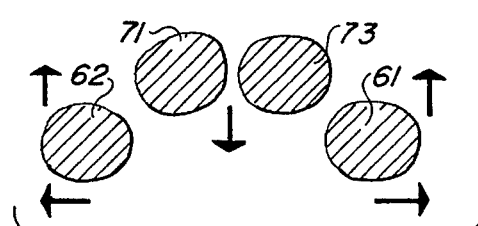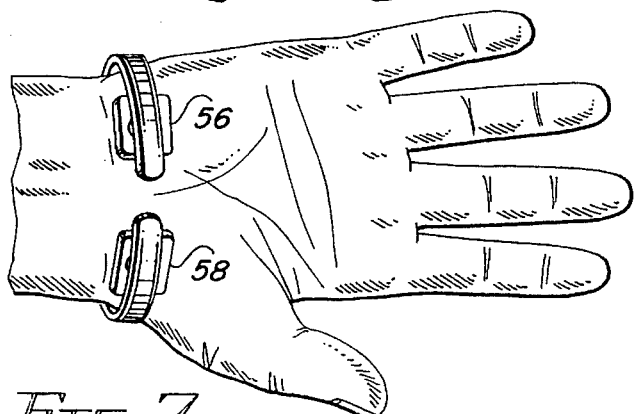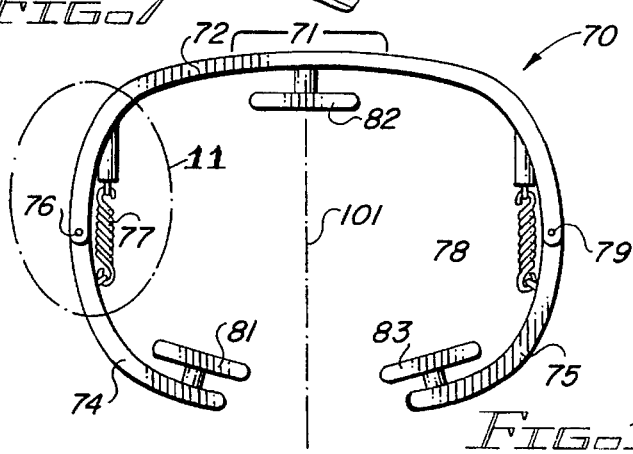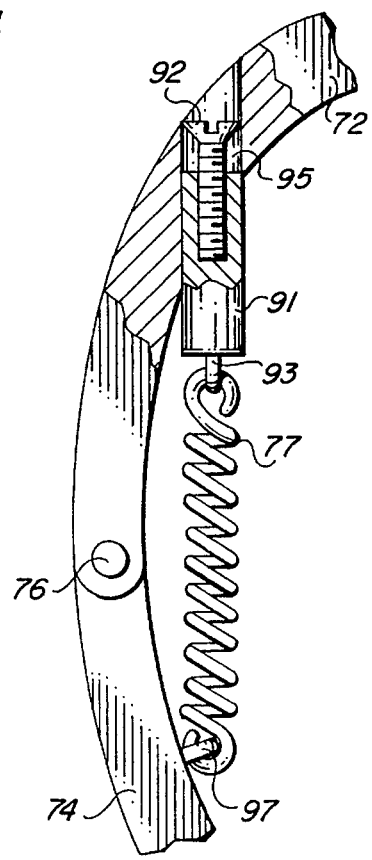

CARPAL TUNNEL BRACELET

BACKGROUND OF THE INVENTION

This invention relates to the treatment or prevention of carpal tunnel syndrome and, in particular, to a bracelet-like appliance for opening the carpal canal by stretching the transverse carpal ligament and the surrounding structure of the hand, wrist, and forearm of a person.

"Carpal Tunnel Syndrome" is the result of a compromised or narrowed carpal canal leading to compression injury of the median nerve in the wrist. The carpal tunnel is the canal in the wrist through which the median nerve and flexor tendons pass from the forearm to the hand. Prolonged, repetitive motion at a keyboard is a common, but by no means the only, cause of the syndrome.

To date, carpal tunnel syndrome has been treated with wrist rests, anti-inflammatory medications, cortisone injections, surgery, or orthoses, such as wrist splints. Alone or combined, these treatments have met with varying degrees of success. The obvious solution, removing the cause of the injury, is not always practical since, as in the case of using a keyboard, the cause of the injury is often the means by which the patient obtains his or her livelihood. The next best choice, prevention through proper preparation, can be achieved by enlarging the carpal canal to maintain adequate space for the median nerve and thus avoid compression.

The carpal canal can be enlarged by osteopathic manipulation and stretching, thereby alleviating compression on the median nerve and resolving carpal tunnel syndrome. While severe cases may require other treatment, manipulation is effective in the majority of cases and has the advantage of being prophylactic, i.e. a preventative.

While manipulation and stretching are effective, there are two difficulties. Optimum resolution of the symptoms requires frequent stretching and the assistance of another person, a physician to perform the manipulation. There is a need for an appliance which a patient can use to augment treatment by the physician. It is known from studies of rehabilitated knee joints and elbow joints that the longest period of low force stretching produces the greatest amount of permanent elongation of connective tissue. Ideally, the stretching would be accomplished by means of an appliance which is adjusted by the physician to provide the appropriate force for stretching, preferably continuously.

Simply prescribing the use of an appliance does not mean that the patient will use it properly. If a patient is expected to put on and remove an appliance, a properly adjusted appliance must not be able to be put on incorrectly or to inflict either too much or too little stretching. Proper use also refers to the compliance or self-discipline of the patient and how easy it is to use the appliance. In general, an appliance that is mechanically simple, easy to use, and comfortable to wear will more likely be used as directed.

The skin is sensitive to long term pressure, which can cause a localized loss of circulation and lead to ulceration. Obviously, a patient will not be comfortable if an appliance causes such irritation. On the other hand, sufficient pressure must be applied in order to be effective.

An appliance must also be comfortable in the sense that it does not interfere with the function of the arm, wrist, and hand. Otherwise, a patient is unlikely to wear the appliance long enough to be fully effective, preferably overnight, or when performing routine tasks which may irritate the median nerve. An appliance duplicating the manipulation by a physician would obviously interfere with the patient's use of the hand. What is desired is an appliance which duplicates as much of the physician's treatment as possible without interfering with the use of the arm, wrist, and hand.

In view of the foregoing, it is therefore an object of the invention to provide a bracelet-like appliance for treating or preventing carpal tunnel syndrome.

Another object of the invention is to provide a mechanically simple, easily used, comfortable appliance for treating or preventing carpal tunnel syndrome.

A further object of the invention is to provide an appliance for relieving the pressure on the median nerve by stretching the transverse carpal ligament and the related or associated structures of the wrist.

Another object of the invention is to provide an appliance which will provide a continuous, gentle pressure for elongating the transverse carpal ligament.

A further object of the invention is to provide an appliance which can be worn continuously despite the fact that the appliance exerts pressure at several locations on the wrist.

Another object of the invention is to provide a bracelet-like appliance for treating or preventing carpal tunnel syndrome wherein the appliance does not impair the function of the arm, wrist, and hand.

SUMMARY OF THE INVENTION

The foregoing objects are achieved in this invention in which it has been found that manipulation and stretching exercise can be successfully augmented by stretching the transverse carpal ligament with a bracelet-like appliance (herein referred to simply as a bracelet) which includes a C-shaped member having a central portion located over the dorsal side of the wrist and two arms encircling the wrist. Each arm has a pad for engaging the palm near the attachment edges of the carpal ligament at the medial or the lateral border of the carpal bones. The bracelet also includes a pad attached to the central portion for engaging the dorsal part of the wrist. The member causes the central pad to press against the dorsal side of the wrist while the ends of each arm press in the opposite direction on the edges of the palm. The result is a gentle flattening of the palm and a lengthening of the transverse carpal ligament. The force applied is preferably 2.0±0.5 pounds if the bracelet is to be worn continuously or for extended periods. The force depends, in part, on the size of the pads and the physical characteristics of the patient. The C-shaped member is a single piece of resilient, malleable material, such as aluminum, or is divided into sections interconnected by spring loaded hinges.

BRIEF DESCRIPTION OF THE DRAWINGS

A more complete understanding of the invention can be obtained by considering the following detailed description in conjunction with the accompanying drawings in which:

FIG. 5 is a dorsal view of a hand with a bracelet constructed in accordance with a preferred embodiment of the invention;

FIG. 6 is a plan view of a bracelet, showing a wrist in cross-section;

FIG. 7 is a ventral view of a hand with a bracelet;

FIG. 8 is a schematic diagram of the forces applied by a bracelet constructed in accordance with the invention;

FIG. 9 is a schematic diagram of the motion produced by a bracelet constructed in accordance with the invention;

FIG. 10 illustrates a bracelet constructed in accordance with an alternative embodiment of the invention;

FIG. 11 is a detail from FIG. 10 showing tension adjustment of a spring; and

DETAILED DESCRIPTION OF THE INVENTION

Several terms are used herein relating to the movement of the fingers and thumb. The fingers and thumb bend or "flex" to grasp a broom handle. If a hand lies with the palm and fingers flat on a flat surface, the fingers are "extended" or straightened. Lifting the fingers, and not the palm, off the surface further extends the fingers. "Abducting" the thumb means moving the thumb away from the fingers while the thumb rests on the surface. "Extension" is lifting the thumb, and not the palm, off the surface. If the forearm also rests on the surface, "extending" the wrist means lifting the palm, and not the forearm, off the surface. These terms relate to the relative movements of the fingers, thumb, palm, and wrist to each other, not to the flat surface. The flat surface is used merely as an aid for visualizing the movements.

Figure 1:
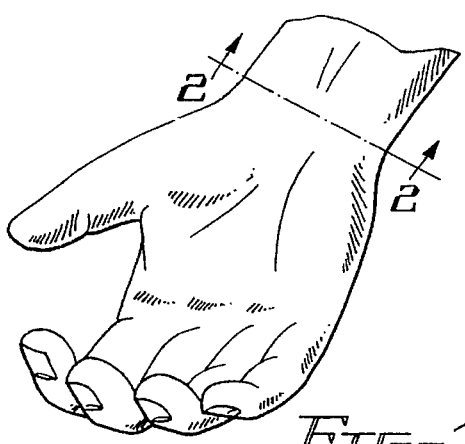
FIG. 1 illustrates the palmar side of a right hand in a relaxed position.
Figure 2:
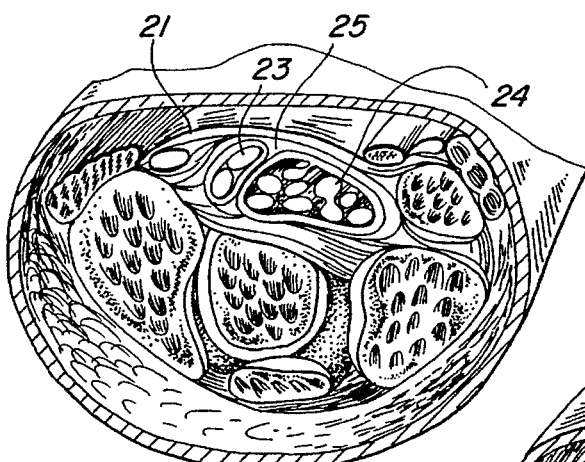
FIG. 2 illustrates a cross-section through the wrist of the hand illustrated in FIG. 1.

Referring to FIGS. 1 and 2, a human right hand in the relaxed position has the fingers flexed slightly, a hollow or concave palm, and the thumb flexed. In the wrist, illustrated in FIG. 2, transverse carpal ligament 21 spans the heel of the hand at the wrist and overlies the carpal canal containing median nerve 23 and flexor tendons 24.

Figure 3:
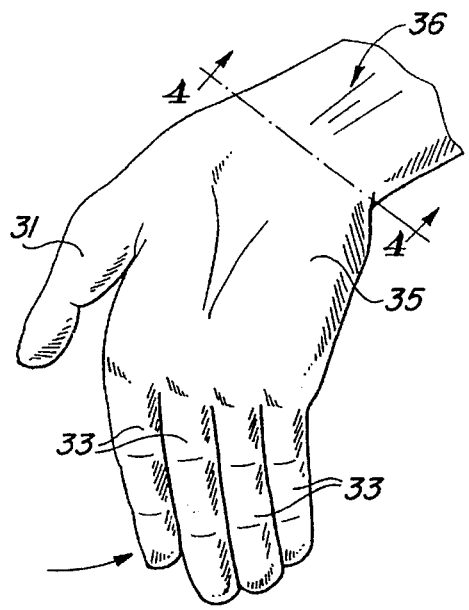
FIG. 3 illustrates a right hand with the thumb, fingers, and wrist extended to stretch the transverse carpal ligament and flexor tendons.

Compression of the median nerve can be relieved by extending the hand as illustrated in FIG. 3. Specifically, thumb 31 is extended and abducted away from the palm, flattening palm 35. Fingers 33 are bent backward relative to palm 35 and the palm is bent backward relative to forearm 36. Thus, the palm is spread open from side to side and from front to back, flattening the palm.

Figure 4:
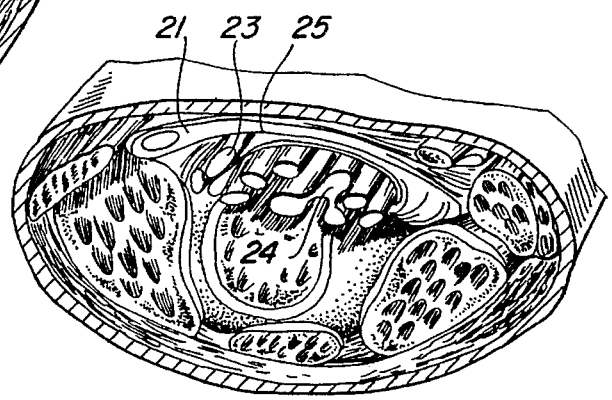
FIG. 4 illustrates a cross-section through the wrist of the hand illustrated in FIG. 3.

Extending the hand, as illustrated in FIG. 3, stretches flexor tendons 24 causing them to elongate and causes the thicker portions of the tendons from the forearm to enter the carpal canal, as illustrated in FIG. 4. The spreading of the palm and the entrance of the thicker portions of the tendons into the canal slightly enlarges carpal canal 25 and thus leads to relief of compression on median nerve 23.

Extending the thicker portions of the tendons into the carpal canal and stretching the transverse carpal ligament cause a transient aggravation of carpal tunnel syndrome since there is a transient increase of pressure within the carpal canal and thus on the median nerve. This may seem to be the opposite of an appropriate maneuver. However, because the carpal canal is also being enlarged, the result of the treatment is a reduction in pressure on the median nerve and reduction or prevention of the symptoms of carpal tunnel syndrome.

The manipulation of the hand as illustrated in FIG. 3 requires a resting place for the patient's fingers and the use of both hands of a physician. It is desired that a continuous treatment be available from a bracelet which supplements manipulation and stretching by a physician.

Because the transverse carpal ligament is a tough, rather unyielding connective tissue, one would not expect it to lengthen without a surgical procedure. A bracelet constructed in accordance with the invention can stretch the transverse carpal ligament. By analogy, bone may appear rigid but Wolff's Law (every change in the form and function of a bone, or in its function alone, is followed by certain definite changes in its internal structure and secondary alterations in its external conformation) explains how even bone tissue can be deformed. "Deform" is being used in the mechanical sense rather than in the aesthetic sense of the word. Bone elements place or displace themselves in the direction of functional forces. Similar effects are known in ligaments.

Surgery provides a radical change in a short time. At present, the transverse carpal ligament is cut rather than lengthened. With the bracelet, the transverse carpal ligament is lengthened slowly over a period of many days. Elongation is not a linear function of time. The initial elongation is greater than the elongation near the end of the treatment. With manipulation and the bracelet, a physician can now provide relief from carpal tunnel syndrome and leave the patient's ligaments intact.

FIGS. 5, 6, and 7 illustrate a bracelet constructed in accordance with a preferred embodiment of the invention. Bracelet 40 includes C-shaped member 41 having central portion 42 interconnecting arm 43 and 44. C-shaped member 41 preferably is made from a malleable material such as soft steel or aluminum. C-shaped member 41 is preferably somewhat resilient or springy and does not deform easily, i.e., does not deform under an applied force of less than 20–25 pounds. As described herein, C-shaped member 41 must exert a force of approximately 2.0±0.5 pounds on the wrist. C-shaped member 41 can be made from any suitable material such as steel, aluminum, or plastic, as long as the force required to deform member 41 is substantially greater than the force to be applied in treatment, e.g. ten times greater.

Pressure pad 51 is attached to C-shaped member 41 at central portion 42. Pressure pad 51 can be attached to central portion 42 by any suitable means such as post 53. Pressure pad 51 is made from a resilient material, such as foam rubber, foam plastic, cloth or cloth-like material, and provides a cushioned contact between C-shaped member 41 and the wrist of a patient. Pressure pad 51 also spreads the force applied from member 41 over an area sufficiently large to prevent irritation of the skin underneath the pressure pad, even if bracelet 40 is worn continuously. The pressure applied to a wrist by bracelet 40 is adjusted by deforming bracelet 40 or by providing pads which are movable relative to C-shaped member 41.

Bracelet 40 includes pressure pad 56, located at the free end of arm 43, and pressure pad 58, located at the free end of arm 44. As shown in FIGS. 6 and 7, pressure pad 56 is located near hamate bone 62 and pressure pad 58 is located near trapezium 61. Pads 51, 56, and 58 compress the wrist between them such that hamate bone 62 and trapezium 61 are spread apart, elongating the transverse carpal ligament.

FIGS. 8 and 9 schematically illustrate the forces applied to a wrist and the resulting motion of the bone. As indicated in FIG. 8 by arrows 64, 65, and 66, capitate bone 71 and trapezoid bone 73 are forced downwardly between hamate bone 62 and trapezium 61. The applied pressure causes the hamate bone 62 to separate from trapezium 61, as illustrated in FIG. 9. It is understood that the relative motion indicated by the arrows in FIG. 9 is exaggerated and that the wrist is flattened only slightly by the appliance.

A treatment continues through a course of weeks during which adjustments are made to the bracelet to insure that the desired pressure is maintained on the wrist. Initially, the patient may return to the physician every couple of days for adjustment of the bracelet. At the end of the treatment, the patient need only be checked about every two weeks to insure effective treatment. The length of treatment depends upon how severe a patient's condition is. A typical treatment may last four to eight weeks. An advantage of the bracelet is that a patient can use a bracelet as a preventative or for maintenance, e.g. by wearing the bracelet intermittently or discontinuously.

FIG. 10 illustrates an alternative embodiment of the invention wherein the bracelet incorporates hinges which are biased closed by a spring and the tension of the spring can be adjusted to provide the correct force on a wrist. Bracelet 70 includes central portion 71 of dorsal section 72 which is connected to arm 74 by hinge 76 and spring 77. Dorsal section 72 is connected to arm 75 by spring 78 and hinge 79. Together, section 72, arm 74, and arm 75 form a C-shaped member for substantially enclosing a human wrist. Pressure pad 81 is attached to arm 74, pressure pad 82 is attached to section 72 at central portion 71, and pressure pad 83 is attached to arm 75. Bracelet 70 works in the same manner as bracelet 40 to provide pressure on the wrist to flatten the palm and elongate the transverse carpal ligament.

The tension in each arm can be adjusted by a screw mechanism as illustrated in FIG. 11. Dorsal section 72 includes holes for receiving connector 91 having an internal thread for receiving bolt 92 which extends through dorsal section 72 to engage connector 91. Spring 77 is attached at one end to eyelet 93 on connector 91 and is attached at the other end to eyelet 97 on arm 74. Connector 91 fits within counterbore 95 and is located within the counterbore by rotating bolt 92 in either direction to move connector 91 along its longitudinal axis within the counterbore. The longitudinal motion of connector 91 lengthens or shortens spring 77 to adjust the tension of the spring.

As illustrated in FIG. 10, bracelet 70 has a bilateral symmetry about center line 101. It is not necessary, for example, that pressure pad 82 be located on center line 101. Pressure pad 82 can be located anywhere a physician deems necessary along dorsal section 72. Since pressure pad 82 acts as the fulcrum of a lever, moving pressure pad 82 to either side will increase the force applied by the shorter arm of the bracelet.

Figure 12:
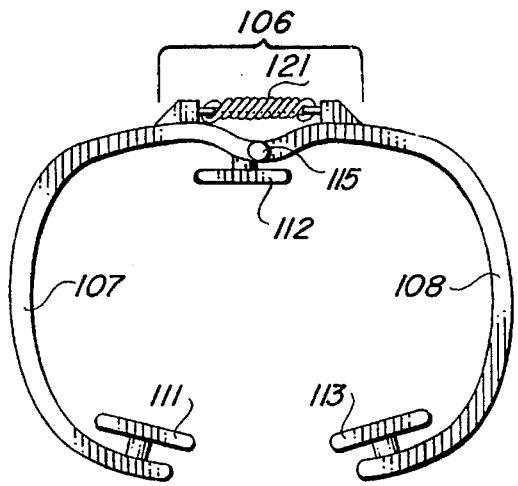
FIG. 12 illustrates a bracelet constructed in accordance with another alternative embodiment of the invention.

FIG. 12 illustrates an alternative embodiment of the invention in which the resiliency of the arms is combined with a spring hinge to provide the desired forces to a wrist. On a wrist, resilient arm 107 applies a force drawing pad 111 toward pad 112 and resilient arm 108 applies a force drawing pad 113 toward pad 112. Resilient arms 107 and 108 are connected at hinge 115 in central portion 106. Arms 107 and 108 are pulled open slightly by tension spring 121, which applies a small sideward component to pads 111 and 113. Friction between the pads and the skin prevents the pads from slipping and the force applied by spring 121 is much smaller than the force applied by arms 107 and 108. The resultant forces on the pads causes a gentle spreading of the trapezium and hamate bones and a stretching of the transverse carpal ligament.

Having thus described the invention it will be apparent to those of skill in the art that various modifications can be made within the scope of the invention. For example, instead of using a separate spring spanning each hinge, one could provide a spring within the hinge for resiliently closing the hinge. Hinges 76 and 79 need not be located at the maximum diameter of bracelet 70, as illustrated in FIG. 10, but can be located closer to pressure pads 81 and 83 to provide a force having a larger component in a direction away from center line 101. The bracelet could be in the shape of a closed loop having a hinge on one side and a tensioning clasp on the opposite side of an elliptical ring. This construction is not preferred because the dorsal pad would no longer be the fulcrum about which the forces on the palm balance. The hinge would act as a fulcrum, putting the palm pads on the same side of the fulcrum. The embodiments of FIGS. 6 and 10 are more easily adjusted than an appliance having a closed loop. The force applied is a matter of discretion with the attending physician. A force of 2±0.5 pounds is preferred for persons of average build.

The invention claimed is:

1. An orthopedic appliance for the treatment or prevention of carpal tunnel syndrome by slowly and gently stretching the transverse carpal ligament over a period of several hours, said appliance comprising:

a C-shaped member having a central portion, a first arm extending in a first direction from said central portion to a free end, and a second arm extending in a second direction, opposite the first, from said central portion to a free end;

a first pad attached near the free end on the interior of said first arm;

a second pad attached near the free end on the interior of said second arm;

a third pad attached to the interior of said central portion;

wherein, when said appliance is worn on a wrist, said third pad presses upon a dorsal part of the wrist while said first pad and said second pad press in the opposite direction on the edges of the palm to flatten the palm and stretch the transverse carpal ligament.

2. The orthopedic appliance as see forth in claim 1 wherein said C-shaped member further includes:

a first hinge connecting said first arm to said central portion;

wherein said first hinge includes a spring for resiliently pushing said first pad toward said third pad.

3. The orthopedic appliance as see forth in claim 2 wherein said C-shaped member further includes:

a second hinge connecting said second arm to said central portion;

wherein said second hinge includes a spring for resiliently pushing said second pad toward said third pad.

4. The orthopedic appliance as set forth in claim 1 wherein said C-shaped member is malleable for changing the force applied by the appliance when worn on a wrist.

5. The orthopedic appliance as set forth in claim 4 wherein the force required for deformation of the bracelet is at least ten times the force applied by the appliance to a wrist.

6. The orthopedic appliance as set forth in claim 1 wherein each pad is attached to said C-shaped member by a post.

7. The orthopedic appliance as set forth in claim 6 wherein the height of each post is adjustable for adjusting the force applied by the appliance when worn on a wrist.

* * * * *